(12) United States Patent
Cosmi et al.

(10) Patent No.: US 11,337,644 B2
(45) Date of Patent: May 24, 2022

(54) METHOD, DEVICE AND MACHINE FOR CALCULATING AN INDEX REPRESENTATIVE OF THE PROPERTIES OF A MATERIAL OF THE BONE TYPE

(71) Applicants: M2TEST S.R.L., Trieste (IT); Università degli Studi di Trieste, Trieste (IT)

(72) Inventors: Francesca Cosmi, Udine (IT); Alessandra Nicolosi, Udine (IT)

(73) Assignees: M2TEST S.R.L., Trieste (IT); Università degli Studi di Trieste, Trieste (IT)

(\*) Notice: Subject to any disclaimer, the term of this patent is extended or adjusted under 35 U.S.C. 154(b) by 340 days.

(21) Appl. No.: 16/734,702

(22) Filed: Jan. 6, 2020

(65) Prior Publication Data
US 2021/0204866 A1 Jul. 8, 2021

(51) Int. Cl.
*G06K 9/00* (2022.01)
*A61B 5/00* (2006.01)
(Continued)

(52) U.S. Cl.
CPC ............ *A61B 5/4509* (2013.01); *A61B 5/004* (2013.01); *A61B 5/0037* (2013.01);
(Continued)

(58) Field of Classification Search
CPC ..... A61B 5/4509; A61B 5/0037; A61B 5/004; A61B 5/0048; A61B 5/7264;
(Continued)

(56) References Cited

U.S. PATENT DOCUMENTS 6,468,215 B1\* 10/2002 Sarvazyan ........... A61B 8/0875
600/449
7,386,154 B2 6/2008 Cosmi
(Continued)

OTHER PUBLICATIONS

Cosmi F. et al. "Evaluation of the structural quality of bone in a case of progressive osteoporosis complicating a Complex Regional Pain Syndrome (CRPS) of the upper limb", Sep. 5, 2013, Journal of mechanical behaviour of biomedical materials, vol. 25, pp. 517-528 (Year: 2013).\*

(Continued)

*Primary Examiner* — Van D Huynh
(74) *Attorney, Agent, or Firm* — Egbert, McDaniel & Swartz, PLLC

(57) ABSTRACT

Method, device and machine for calculating an index representative of properties of a material of the bone type of an individual to be subjected to tests, particularly wherein the method includes a first acquisition step for acquiring at least one image having a plurality of elementary units of a sample of the material, wherein a generation step is provided for generating a grid of elementary geometric elements, or cells, which is associated with, in particular superimposed on, the image, an image processing step in which it is provided to calculate at least the apparent elastic modulus and a density coefficient of the material, both as a function of characteristic values of each cell, and a calculation step for calculating the index representative of the properties of a material, wherein the index is a function of the value of the apparent elastic modulus net of the contribution of the density coefficient.

24 Claims, 9 Drawing Sheets

(51) Int. Cl.
  *G16H 15/00* (2018.01)
  *G06T 7/00* (2017.01)

(52) U.S. Cl.
  CPC .......... *A61B 5/0048* (2013.01); *A61B 5/7264* (2013.01); *G06T 7/0012* (2013.01); *G16H 15/00* (2018.01); *G06T 2207/10116* (2013.01); *G06T 2207/20081* (2013.01); *G06T 2207/20084* (2013.01); *G06T 2207/30008* (2013.01)

(58) Field of Classification Search
  CPC ......... G06T 7/0012; G06T 2207/10116; G06T 2207/20081; G06T 2207/20084; G06T 2207/30008; G06T 2207/20021; G16H 15/00; G06F 30/20; G06F 30/23; G06F 30/27; G06F 2111/10
  USPC ....................................................... 382/128
  See application file for complete search history.

(56) References Cited

U.S. PATENT DOCUMENTS

| | | | | |
|---|---|---|---|---|
| 2002/0196966 | A1* | 12/2002 | Jiang | G06T 7/0012 382/132 |
| 2005/0117788 | A1* | 6/2005 | Cosmi | G06T 17/20 382/128 |
| 2012/0232375 | A1* | 9/2012 | Zebaze | G06T 7/70 600/407 |
| 2014/0126800 | A1* | 5/2014 | Lang | G06T 7/0012 382/132 |
| 2018/0247020 | A1* | 8/2018 | Itu | G06N 20/00 |
| 2021/0153823 | A1* | 5/2021 | Schildkraut | A61B 6/461 |

OTHER PUBLICATIONS

Cosmi F. et al., "Implementation of correctness criteria for the bone structure analysis by means of a hand-held X-ray system", Sep. 19, 2017, 34th Danubia-Adria Symposium on advances in experimental mechanics, University of Trieste, Italy (Year: 2017).*

Anonymous: "Lone Oak Medical Technologies Technical Product Brief—accudxa2 Model 7200 BMD Assessment System", Jan. 1, 2011 (Jan. 1, 2011), pp. 1-3, XP055781419, Retrieved from the Internet: URL: https//jdhmedical.com/wp-content/pdf/accudxa2%20Product%20Technical%20Description.pdf (Year: 2011).*

Dhainaut A. et al.,"The ability of hand digital X-ray radiogrammetry to identify middle-aged and elderly women with reduced bone density, as assessed by femoral neck dual-energy X-ray absorptiometry", 2010, J Clin Densitom. vol. 13 (4), 418-425.

Alenfeld, F. E. et al., "Ultrasound Measurements at the Proximal Phalanges in Healthy Women and Patients with Hip Fractures", 1998, Osteoporosis Int. 8(5), 393-398.

Cosmi F. et al."Evaluation of the structural quality of bone in a case of progressive osteoporosis complicating a Complex Regional Pain Syndrome (CRPS) of the upper limb", Sep. 5, 2013, Journal of mechanical behaviour of biomedical materials, vol. 25, pp. 517-528.

Cosmi F. et al., "Implementation of correctness criteria for the bone structure analysis by means of a hand-held X-ray system", Sep. 19, 2017, 34th Danubia-Adria Symposium on advances in experimental mechanics, University of Trieste, Italy.

* cited by examiner

METHOD, DEVICE AND MACHINE FOR CALCULATING AN INDEX REPRESENTATIVE OF THE PROPERTIES OF A MATERIAL OF THE BONE TYPE

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to a method, a device and a machine for calculating an index representative of the properties of a material of the bone type, starting from at least one image of a sample of such material, in accordance with the appended claims.

2. Description of Related Art Including Information Disclosed Under 37 CFR 1.97 and 37 CFR 1.98

The study of the structural resistance of materials is an extremely complex science having significant implications in various sectors, such as in mechanical engineering, in the building sector or in bioengineering. Designing a mechanical component or the structure of a building needs accurate studies aimed at assessing the statics of the structure to ensure suitable resistance to planned loads. Accurate designing allows to predict which would be the behaviour of a structure subjected to given loads, in order to prevent fractures or damage of the structure itself.

In the biological sector as well as in industrial applications complex materials are often used, whose mechanical properties do not depend only on the percentage of presence of a resistant phase but are the result of the spatial arrangement of the phase itself as well.

Over the years these principles have also been used to study the resistance of bone materials for the purpose of assessing the resistance of the bone tissue with a good degree of precision. The bone tissue has a very complex structure formed by an internal "trabecular" structure consisting of elements called trabeculae and enclosed in an external "cortical" structure.

However, in order to study the resistance of the bone tissue, it is not sufficient to know only its composition and density because the elasticity and the resistance of the bone tissue depend on the conformation of the bone material. In particular, it has been observed that the elasticity and the resistance of the bone tissue significantly depend on the capability of the trabecular structure to bear loads, that is to say, on the quality of the trabecular structure.

Scientific literature comprises many publications that report a direct correlation between the presence of alterations of the hand's bone structure and the structural resistance of an individual's bone tissue. For example, the publication entitled "The ability of hand digital X-ray radiogrammetry to identify middle-aged and elderly women with reduced bone density, as assessed by femoral neck dual-energy X-ray absorptiometry", by Dhainaut A. et al., 2010, J Clin Densitom. 13(4), 418-425, describes a correlation between the radiologic analysis of the hand's bone and the presence of alterations of the individual's bone structure, which are indicative of the presence of possible diseases. Likewise, the publication entitled "Ultrasound Measurements at the Proximal Phalanges in Healthy Women and Patients with Hip Fractures", by Alenfeld F. E. et al., 1998, Osteoporosis Int. 8(5), 393-398, too, describes a correlation between the ultrasound analysis of the bones of the hand's proximal phalanx and the presence of alterations in the individual's hip.

The document "Evaluation of the structural quality of bone in a case of progressive osteoporosis complicating a Complex Regional Pain Syndrome (CRPS) of the upper limb", Cosmi F. et al., Journal of mechanical behaviour of biomedical materials, Vol. 25, 5 Sep. 2013, pages 517-528, describes a solution for performing a test for simulating the application of compression loads on a structure of trabeculae extracted from a digital X-ray in the case of an individual affected by a serious form of localised bone alteration, in this case spotty osteoporosis, different from age-related osteoporosis.

The document "Implementation of correctness criteria for the bone structure analysis by means of a hand-held X-ray system", Cosmi F. et al., 34th Danubia-Adria Symposium on advances in experimental mechanics, University of Trieste, Italy, 19 Sep. 2017, describes a hand-held device for taking digital X-rays of a patient, in particular of a patient's hand, suggesting the use of a support of the radiographic detection tool and of a support for the sensitive element to be applied in the measuring zone consisting of a finger.

A method for assessing the mechanical response of any material, including bone tissue, in relation to the particular conformation assumed by the phases making up the material being examined, is described by the U.S. Pat. No. 7,386,154 B2.

In accordance with what is disclosed in this patent, it is provided to transform a digital or digitalised image, for example detected by a radiographic device known in the art, into a numerical model that allows to carry out processing by applying the so-called "Cell method" (CM).

As a result of the processing, it is possible to know both the elastic response of the architecture reconstructed in the model and the normalised sum of the levels of grey detected in the radiographic image, which in the case of a bone structure is indicative of the mineralisation of the bone structure being examined.

Problems of the Prior Art

A drawback of the method described in U.S. Pat. No. 7,386,154 B2 lies in the fact that the results of the processing, although deriving from reliable and accurate calculations, are unsuitable for a classification of the quality of the bone structure analysed.

Aim of the Invention

In particular, an aim of the present invention is to provide a method for calculating an index that is usable and easy to be interpreted and that classifies, amplifying them, the differences induced by different internal architectures on the mechanical properties of a material of the bone type.

Another aim of the present invention is to provide a method that can employ the equipment normally available in laboratories or in radiologic centres and that is easy to be performed by the operator.

Another aim of the present invention is to provide an image acquisition system allowing an operator to acquire the best possible image.

In particular, an aim of the present invention is to provide a measuring device that is compact, portable and easy to use and that allows to keep still, in the planned position, a patient's anatomical site in a steady and effective way.

A further aim of the present invention is to provide an easy-to-use measuring machine that allows to keep still, in the planned position, a patient's anatomical site in a steady and effective way and that enables automatic measuring.

BRIEF SUMMARY OF THE INVENTION

The aim of the invention is achieved by the characteristics of the main claim. The sub-claims represent advantageous solutions.

In accordance with said aims, the present invention relates to a method for calculating an index representative of the mechanical properties of a monophase or multiphase material, comprising an initial acquisition step for acquiring at least one image of a sample of the material, the image allowing to distinguish from each other the one or more phases object of the study inside a closed region of interest, in which the subsequent processings will be carried out.

According to some embodiments disclosed herein, the method comprises a generation step for generating a grid of elementary geometric elements, or cells, which is associated with, in particular superimposed on, the image, and a step in which, for each of the cells covering the region of interest, it is provided to acquire a parameter indicative of the presence or absence in the cell of the phase considered (for example the bone phase) and—in the event in which the phase is present—proportional to the quantity of the phase present in the cell.

In some embodiments the method includes an image processing step, in which it is provided to calculate a density coefficient of the material as a function of characteristic values of each cell, calculated on the basis of the value(s) of said parameter indicative of the phases falling within the cell; wherein the density coefficient, for each region of interest, is a univocal value calculated as the sum of the parameters involved. According to some embodiments the image processing step also provides to calculate the value of the apparent elastic modulus by means of simulations of the behaviour under load resulting from the application of modes known in the art, in which the mechanical behaviour of the internal structure of the region of interest is simulated, to which each cell contributes with its own value of apparent elastic modulus and of said parameter.

According to a characteristic aspect of the present invention, the method comprises a calculation step for calculating the index representative of the properties of a material, wherein the index is proportional to the value of the apparent elastic modulus net of the contribution of said density coefficient, both of which are suitably weighted.

In an embodiment, in the first acquisition step, it is provided to acquire three images of samples to be analysed; and to repeat the processing step for each image acquired, thus obtaining at least one value of apparent elastic modulus and one value of density coefficient for each image; a calculation step for calculating the respective values being then provided.

According to some embodiments disclosed herein, after the acquisition step, a pre-treatment step for pre-treating the image acquired is then provided, in which suitable filters are applied to the image in order to better highlight the structure to be examined. Furthermore, a rotation step is provided for rotating the image by such a quantity that a longitudinal direction of extension of the elementary units is substantially parallel to respective horizontal (X) and vertical (Y) directions arranged in such a way as to define the Cartesian axes of the plane (X-Y).

According to some embodiments disclosed herein, after the image pre-treatment step, a definition step is provided for defining the region of interest, defined as the largest square or rectangular area that is fully inscribed in the sample of material being analysed.

In a preferred embodiment the processing step implements the well-known Cell Method (Tonti, E. CMES, 2, 237-258), in which each cell is of triangular shape and has three characteristic nodes in correspondence of the vertices of the triangle.

According to some embodiments the calculation of the apparent elastic moduli ($E^*$) and of the density coefficient (C) is performed according to what is disclosed in U.S. Pat. No. 7,386,154 B2, which is included for reference herein.

An advantage of the method according to the present invention consists in calculating an index that allows to distinguish between different structures having some mechanical properties different from one another (for example a different elastic modulus) against other similar characteristic properties.

Advantageously, thanks to the fact that the contribution of the density coefficient of the structure is separated from the calculation of the elastic modulus, the representative index allows to significantly emphasize such differences, thus constituting an index that is readily and easily interpreted by operators.

In other words, by removing the contribution due to density, which is indicative of the quantity of bone phase, the contribution due to the elastic modulus provided by the organization in space of the material is emphasized, which is symptomatic of the quality of the structure constituting the bone material, that is to say, of its resistance.

Thanks to the fact that the images acquired in the first step are relative to an orderly structure, for example formed by trabeculae arranged parallel to each other according to longitudinal planes connected to each other by further trabecular elements arranged orthogonally to said planes, the calculation of the index representative of the mechanical properties of the material is a much more effective and sensitive parameter with respect to the prior art to distinguish between structures having different levels of the property examined, with respect to the parameter that is directly obtainable from simulations. In fact, Wolff's law states that the arrangement of the trabecular structure is closely linked to the arrangement of the loads normally acting in the anatomical site itself. Fingers are subject to loads acting mainly in a longitudinal direction, which determines said characteristic "orderly" arrangement of the trabeculae. In other anatomical sites subject to combinations of more complex loads, such as the vertebral structure or the femoral head in which, in addition to the longitudinal loads, significant flexural and torsional components are present, the arrangement of the trabecular structure is more complex and is not suitable—for the purpose of the present invention—to be used for the subsequent processings.

Starting from the images acquired, the method allows to reconstruct a two-dimensional model of the structure able to closely approximate the real three-dimensional structure of the sample to be analysed in order to classify the different mechanical behaviour of the structures. In other words, the method according to the present invention advantageously allows to process a two-dimensional image in less time and with less computational burden with respect to the original three-dimensional structure, without jeopardizing the accuracy and reliability of the calculation.

It should be noted that such advantages are much more evident the more orderly the structure of the phase considered is, for example if it is formed by a three-dimensional matrix of elements whose longitudinal direction of extension is substantially parallel to a direction defined by a respective axis included in a set of three Cartesian axes. It was observed that in such orderly structures, such as the internal trabecular structure of the bone tissue in fingers, the method according to the present invention is particularly effective.

According to another characteristic aspect of the present invention, it is provided to use the above-described method to calculate an index representative of the properties of the bone phase in order to predict, and prevent, possible alterations of the bone material of an individual to be subjected to tests, so as to inform the specialized medical staff about individuals who should be considered at risk.

In particular, in this employment, said image acquisition step provides to acquire three digital radiographic images in anterior-posterior projection of the first proximal epiphysis respectively of the three central fingers (index, middle, ring finger) of the non-dominant hand of an individual to be subjected to tests, in correspondence of which the trabecular structure of the bone tissue comprises trabeculae oriented according to planes parallel to each other and to the directrix (X-Y) and staggered in such a way as to be arranged in succession after one another and connected by further trabeculae mainly arranged along a third direction (Z).

An advantage of this employment of what is disclosed in the present invention is that the image acquisition step is little invasive because the images to be acquired are images of an anatomical site (the patient's hand), which allows an easy and fast detection thereof.

It was observed that the index representative of the mechanical properties of a material is extremely useful to detect weakening of the bone structure related to several diseases.

For example, it was observed that performing the method according to the present invention, in accordance with said use, is advantageous to detect the increased risk of fracture in individuals suffering from some diseases or undergoing, for example, some therapies. As a non-exhaustive example, one can mention anti-cancer therapies (in particular for breast cancer or prostate cancer), cancers leading to a decrease in bone resistance, diabetes, rheumatic diseases like arthrosis, therapies with corticosteroids and other drugs that notoriously affect bone resistance.

In these cases, it is well-known that the disease itself, and/or the treatments for combating it, may weaken the bone material, which then can break more easily.

Thanks to said use of the method according to the present invention it is also possible to identify individuals predisposed to undergoing stress fractures due to excessive load, in particular in sports medicine, it thus being advantageously possible to subject athletes to preventive screening tests.

Thanks to said use of the method it is possible to assess the effects, in terms of alterations of the bone structures, consequent to prolonged modifications of the loads normally bearing on the bone structure of an individual to be subjected to tests. For example, said use allows to assess the effects on the bone structure of a long permanence in microgravity conditions (for example in the case of an astronaut), or of long hospitalization forcing an individual to lie down for a long period of time, or still of a modified and more intensive physical training programme.

Thanks to said use of the method according to the present invention it is also possible to assess the capability by the bone structure to bear loads in the application of dental implants also for the purpose of choosing the most suitable type of implant.

Finally, said use of the method according to the present invention is particularly advantageous in the paediatric sector, thanks to the previously mentioned advantages concerning the fact that the method is not invasive and that the first image acquisition step can be performed easily and rapidly.

According to another aspect of the present invention, a detection system is provided for detecting images of a sample of material to be analysed comprising a portable device comprising a handle for the operator, which is connected to a body provided with X-ray emitting means with which screening means are associated, which are configured to screen the operator from the radiation produced by the X-ray emitting means, a support base configured to support in a stable way the portable device, at least during the first acquisition step for acquiring the digital images of said sample of material to be analysed, and sensor means intended to be associated, in use, with the anatomical site being analysed to detect the X-rays emitted by the X-ray emitting means.

According to a preferred embodiment the sensor means are of the digital type.

In an embodiment the sensor means can be integrated in an annular band intended to be wrapped around one finger or one hand of the patient.

According to another aspect of the present invention a detection system is provided for detecting images of a sample of material to be analysed, comprising a detection machine of the fixed type.

An advantage of the present invention consists in providing a detection system facilitating the acquisition of good-quality images by the operator because, thanks to the configuration of the support base, the portable device is supported in a stable way so as to acquire a good-quality image of a sample of material to be analysed, for example a patient's non-dominant hand.

Another advantage of the present invention consists in ensuring the correct positioning of the anatomical site being examined, for example a patient's finger, with respect to the detection system during image acquisition. In fact, thanks to the proximity between the operator and the patient, the operator can immediately notice unintentional movements of the patient, which may jeopardize the quality of the image acquired.

Another advantage of the present invention consists in providing a detection device improving the patient and operator's safety, by minimizing their exposure to X-rays.

In fact, the patient is advantageously hit by a significantly smaller quantity of X-rays with respect to other methods for detecting images of anatomical sites known in the art. For example, the method according to the present invention allows to emit an amount of radiation that is much smaller than the one normally hitting the patient when performing a conventional bone densitometry test.

These and other aspects, characteristics and advantages of the present disclosure will be more evident with reference to the following description, to the drawings and to the claims attached. The drawings, which are integrated in and are part of the present description, illustrate some embodiments of the present invention and, along with the description, aim at describing the principles of the disclosure.

The various aspects and characteristics described in the present description can be applied individually, where possible. These individual aspects, such as aspects and characteristics present in the description or in the dependent claims enclosed, may be the subject of divisional applications.

It should be noted that any aspect or characteristic that is already known during the patenting procedure is meant to be not claimed and to be the subject of a disclaimer.

Advantageous Effects of the Invention

The solution in compliance with the present invention, through its considerable creative contribution, the effect of which constitutes immediate and non-negligible technical progress, has various advantages.

An advantage of the method according to the present invention consists in allowing to calculate an index that enables a distinction between different structures having some mechanical properties different from each other, such as a different elastic modulus, against other similar characteristic properties.

Advantageously, thanks to the fact that the contribution of the density coefficient of the structure is separated from the calculation of the elastic modulus, the representative index allows to significantly emphasize such differences, thus constituting an index that is readily and easily interpreted by operators.

An advantage of the present invention is to provide a detection system allowing the acquisition of good-quality images by the operator or even automatically.

Another advantage of the present invention is to ensure the correct positioning of the anatomical site being examined.

Another advantage of the present invention is to provide a measuring machine and device improving the patient and operator's safety, by minimizing their exposure to X-rays.

Definitions

The term "phase" referred to a material, in the context of the present invention, refers to the usual meaning attributed to such term in materials science, that is to say, to the elements constituting the material, each identified by specific chemical and physical characteristics. For example, in a structural sample of concrete it is possible to find one phase consisting of cement and one phase consisting of gravel or sand. In still another example, in a portion of the human body, it is possible to find a bone phase, a muscle phase and a liquid phase such as for body fluids like blood.

BRIEF DESCRIPTION OF THE SEVERAL VIEWS OF THE DRAWINGS

In the following an embodiment is described with reference to the drawings enclosed, which are to be considered as a non-limiting example of the present invention, in which.

DETAILED DESCRIPTION OF THE INVENTION

Figure 1:
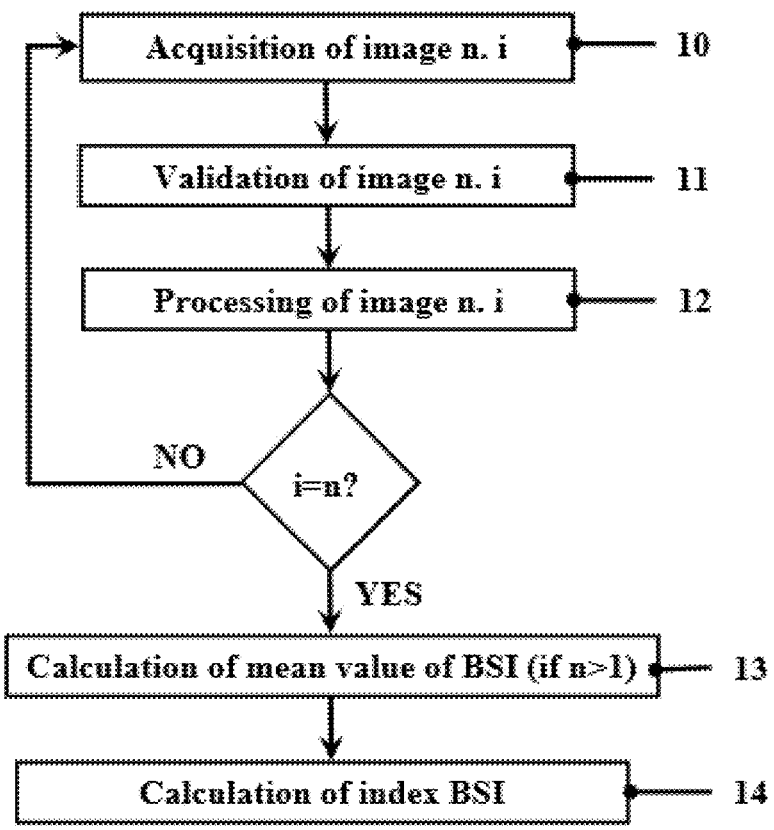
FIG. 1 is a block diagram of an embodiment of a method according to the present invention.
Figure 2:
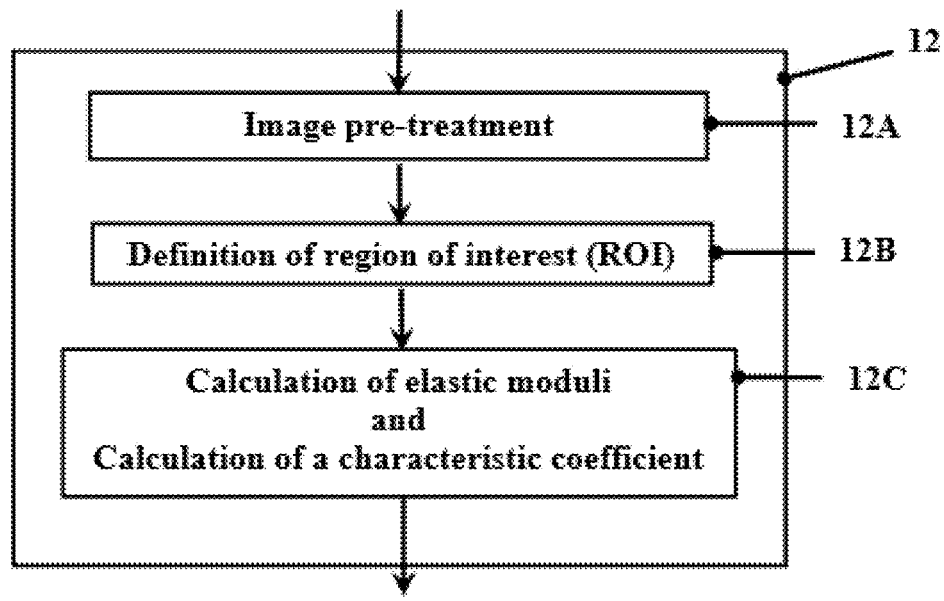
FIG. 2 is a detail view concerning a processing step included in the block diagram of FIG. 1.

In the figures (FIG. 1, FIG. 2) one can see a block diagram illustrating the various steps of the method according to the present invention. The method comprises an acquisition step (10) for acquiring at least one image "i", preferably of a series of images "i" wherein "i" indicates an integer corresponding to an index of each of the images acquired. Each of the images acquired is a representative image of the structure to be analysed.

Figure 16:
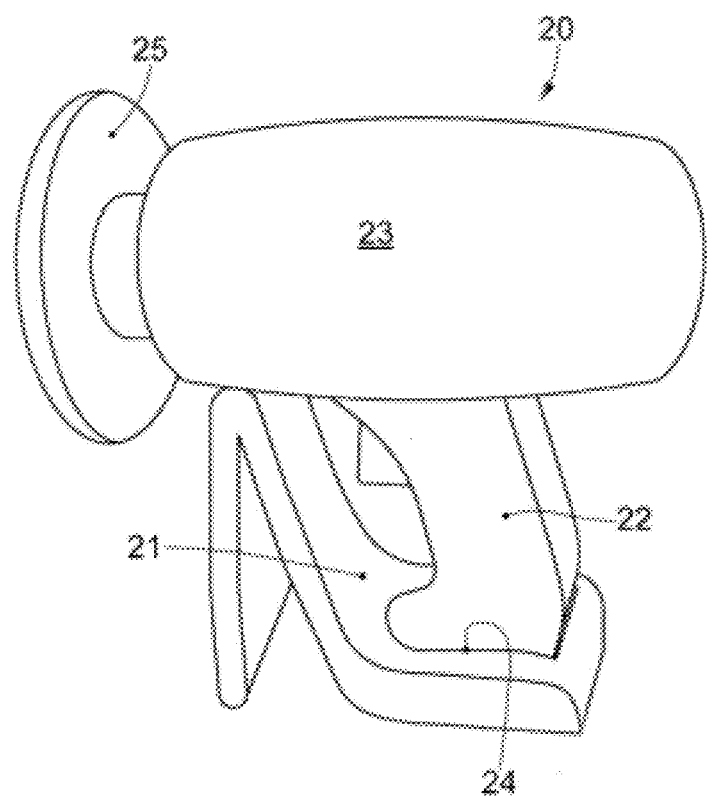
FIG. 16 and FIG. 17 are schematic perspective views of two embodiment variants of a detection system according to the present invention suitable to implement a method according to FIG. 1 by using a measuring system made in the form of a portable device.
Figure 17:
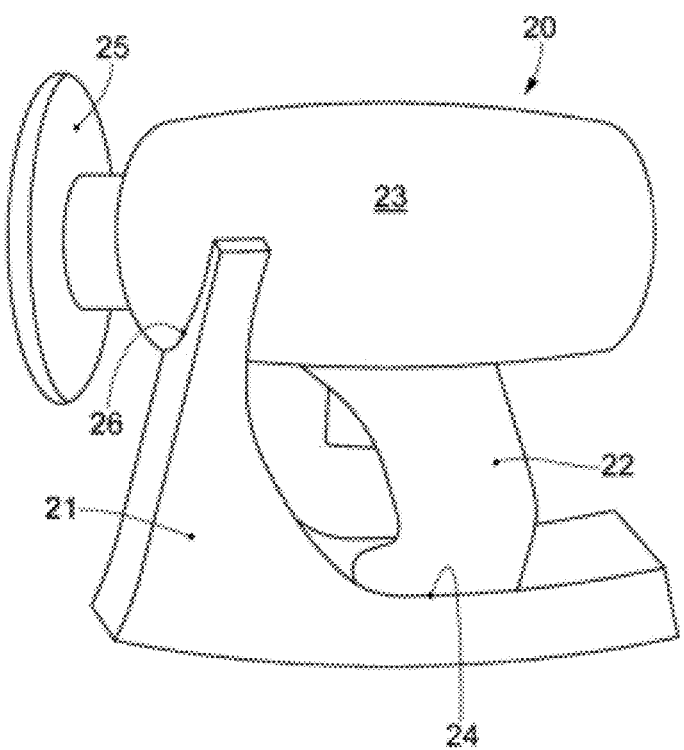
Figure 18:
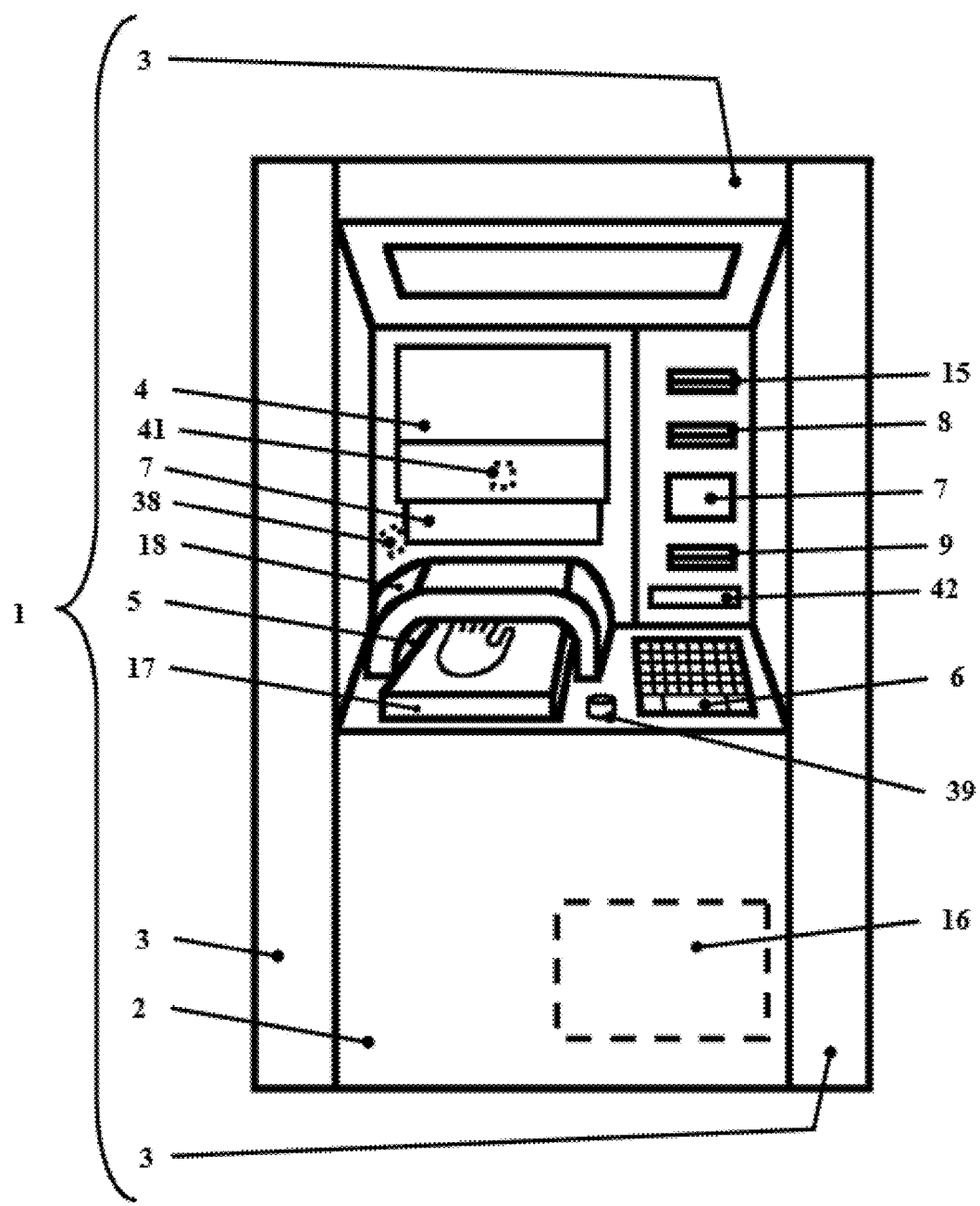
FIG. 18, FIG. 19, FIG. 20, FIG. 21 are schematic perspective views of two embodiment variants of a detection system according to the present invention suitable to implement a method according to FIG. 1 by using a measuring system made in the form of a machine of the fixed type.
Figure 19:
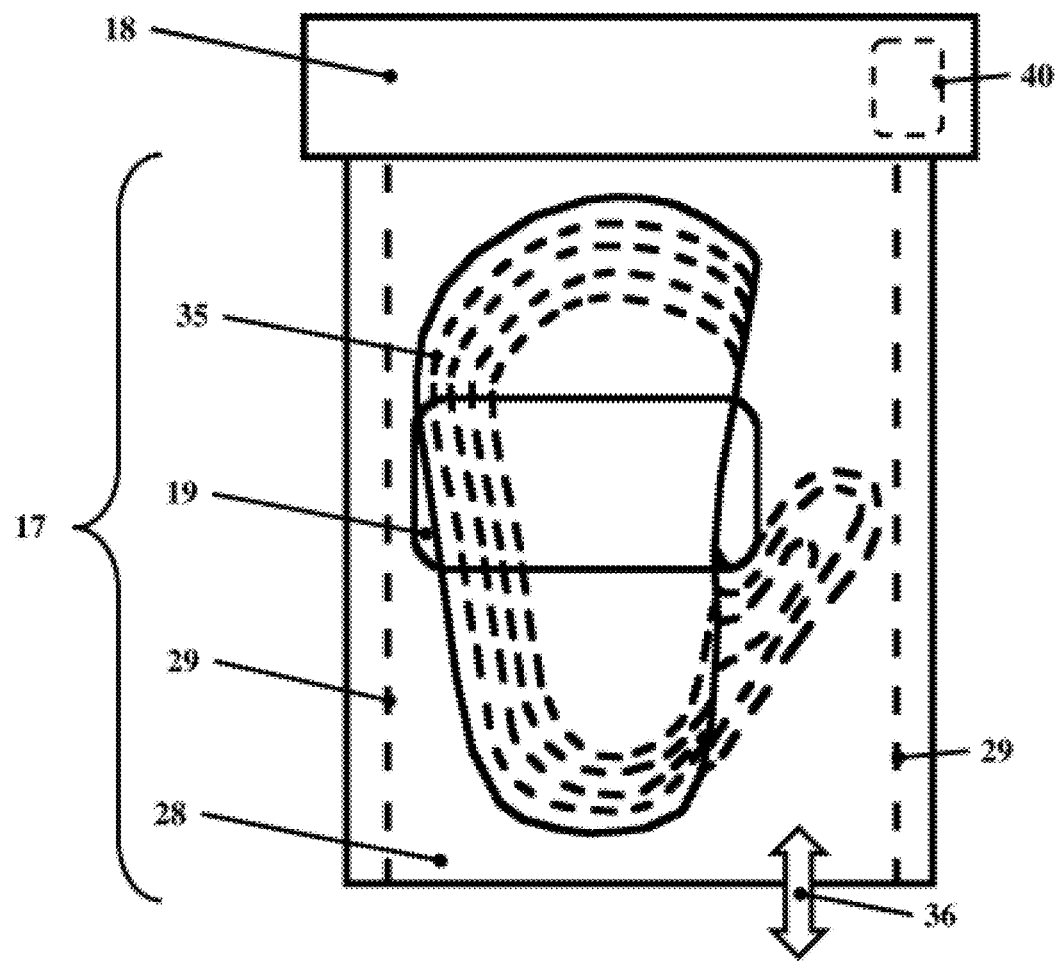
Figure 20:
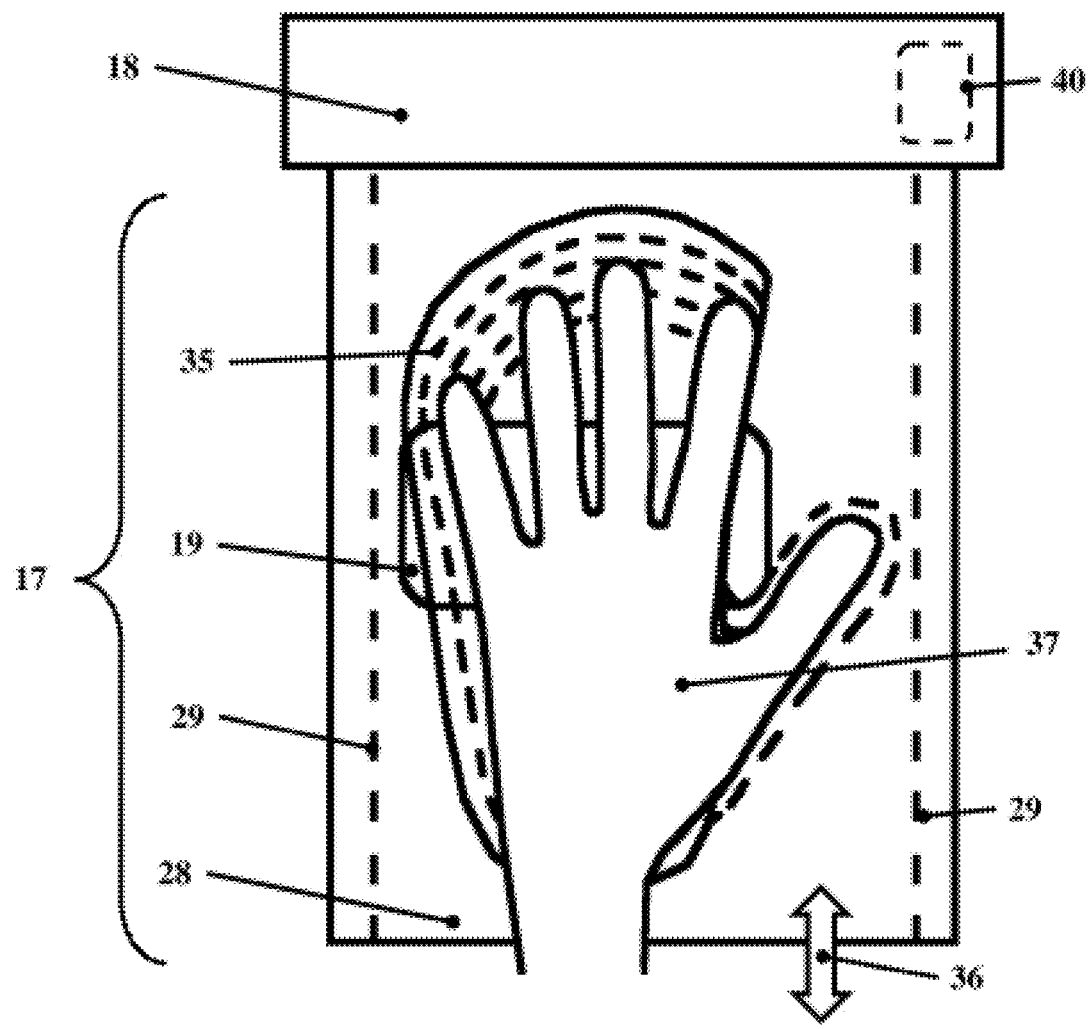
Figure 21:
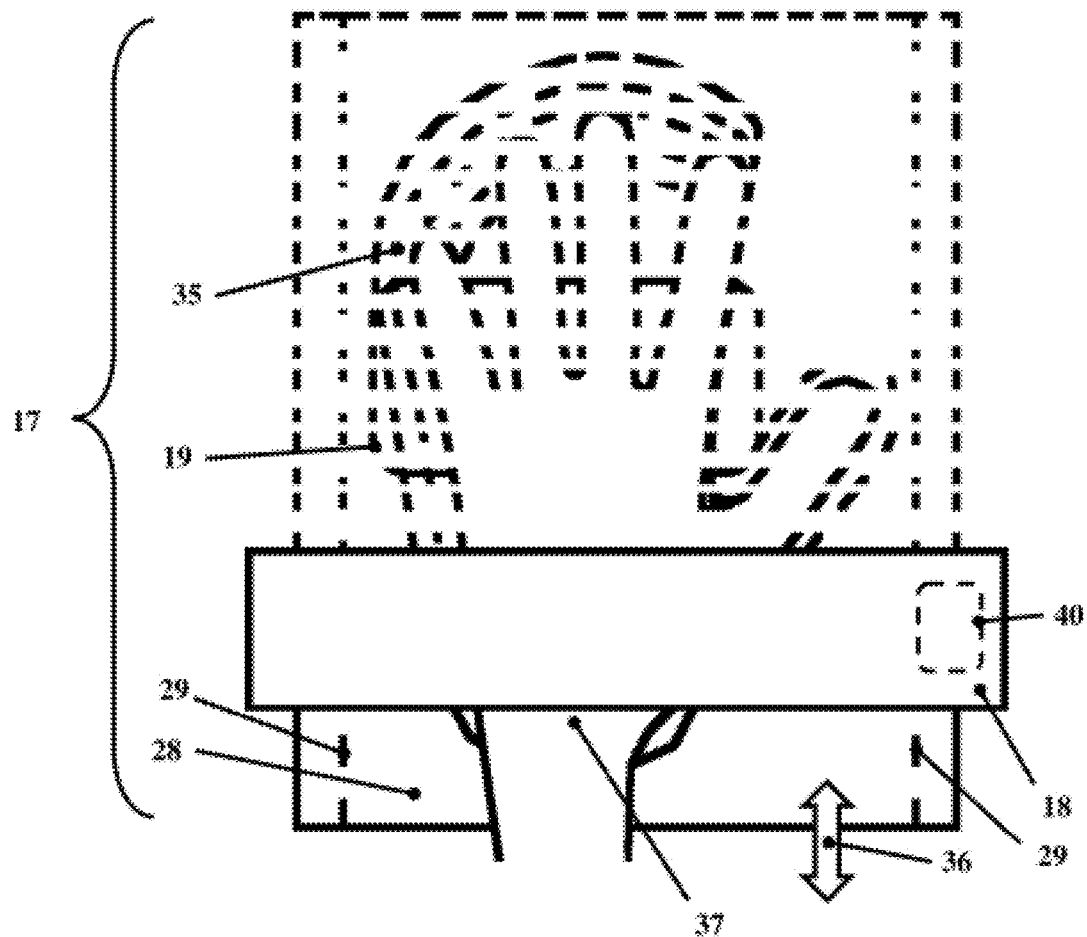

In a preferred embodiment the images can be acquired by means of a detection system that can be (FIG. 16, FIG. 17) a portable measuring device (20) or (FIG. 18, FIG. 19, FIG. 20, FIG. 21) a measuring machine (1), wherein the portable measuring device (20) and the measuring machine (1) operate in accordance with what is disclosed in the present invention, which will be described in further detail hereinafter with particular reference to the figures.

In an embodiment (FIG. 1) the method comprises a validation step (11) in which it is provided to validate the image or images acquired in the acquisition step (10). In a preferred embodiment the validation step (11) of the images provides to check the matching of the images with respect to reference standards, for example at least in terms of format and size.

Afterwards, the method comprises (FIG. 1, FIG. 2) a processing step (12) for processing the images acquired in the acquisition step (10), after the optional validation step (11).

According to an embodiment the processing step (12) comprises (FIG. 2) a pre-treatment sub-step (12A) for pre-treating the image acquired, a definition sub-step for defining the ROI (12B), which is the acronym for "Region Of Interest", in which the subsequent processings will be carried out, and a calculation sub-step (12C), which will be described in further detail hereinafter.

According to an embodiment in the pre-treatment sub-step (12A) for pre-treating the image the image is rotated after being suitably filtered by using, for example, a "sub-threshold erosion non-linear filter" according to techniques known in the art.

According to an embodiment in the definition sub-step for defining the ROI (12B) the region of interest is defined as the largest square area that can be fully inscribed in the acquired image of the structure to be analysed. According to an alternative embodiment the region of interest has predetermined and constant dimensions. In an embodiment the region of interest can be rectangular and substantially coincide with the most external perimeter of the acquired image of the structure to be analysed.

Since the region of interest is generally square or rectangular, in the pre-treatment sub-step (12A) for pre-treating the image acquired the image is rotated in such a way that the two main axes of the structure to be analysed, that is to say, the Cartesian axes X and Y, which are orthogonal with respect to each other, are parallel to respective adjacent sides of the region of interest, arranged perpendicularly to each other.

According to an embodiment in the calculation sub-step (12C) the apparent elastic modulus $E_x^*$, $E_y^*$ is calculated in the directions X and Y, respectively, according to what is disclosed in U.S. Pat. No. 7,386,154 B2. Thus, it is provided to add up the apparent elastic moduli $E_x^*$, $E_y^*$ in the two directions X and Y.

According to an embodiment in the calculation sub-step (12C) the density coefficient (C) is also calculated, which, in the case of bone material, is indicative of the local level of mineralisation of the bone phase in the region of interest, and is directly proportional to the sum of the levels of grey of the image acquired.

In a preferred embodiment the density coefficient (C), too, is calculated according to what is disclosed in the above-mentioned U.S. Pat. No. 7,386,154 B2 as the summation of the values of the indices ($I_{CELL}$) assigned to each cell of the model, for all the cells.

According to embodiments said pre-treatment sub-step (12A), ROI definition sub-step (12B), calculation sub-step (12C) can be alternatively performed manually or automatically.

After performing the processing step (12), the method (FIG. 1) provides a calculation step for calculating mean values (13), averaged over the number of images acquired. In fact, it is evident that, if several images are acquired, for each of them it is provided to repeat the validation step (11) and the processing step (12), then calculating the average of the parameters calculated.

According to embodiments it is provided to calculate the mean value respectively of the sum of the apparent elastic moduli $E_x^*$, $E_y^*$ and of the density coefficient (C), which have been previously calculated.

It is evident that, in case only one image has been acquired, the calculation step for calculating the mean values (13) can be omitted.

After performing the calculation step for calculating the mean values (13), the method then provides a calculation step (14) for calculating the index representative of the properties of the materials.

According to an embodiment the representative index, herein called BSI, which is the acronym for "Bone Structure Index", is calculated according to the following formula:

$$BSI=f[f_1(E^*)-f_2(C)]$$

in which f, $f_1$ and $f_2$ are functions that are different from each other, not necessarily linear, and in particular:
  f is a function of the exposure parameters used during the first image acquisition step;
  $f_1$ and $f_2$ are functions whose result (for each of them) is a constantly positive value so that the result of $f_2$ is actually subtracted from $f_1$.

It should be noted that, since $f_1$ and $f_2$ are constantly positive functions, the formula for calculating the index BSI allows to subtract the contribution due to the density of the material to the contribution due to the elastic modulus.

According to a simplified embodiment the representative index, herein called BSI, which is the acronym for "Bone Structure Index", is calculated according to the following formula:

$$BSI=a_1(b_1E^*-b_2C)$$

where:
  $a_1$ is a value function of the exposure parameters used during the first image acquisition step, while $b_1$ and $b_2$ are positive constants,
  $E^*$ is the apparent elastic modulus (apparent Young's modulus), and
  C is the density coefficient.

It should be noted that, since $b_1$ and $b_2$ are positive constants, the formula for calculating the index BSI allows to subtract the contribution due to the density of the material to the contribution due to the elastic modulus. In an embodiment, after the calculation step (14) for calculating the representative index, a comparison step is optionally provided, in which the calculated index BSI is compared with a reference value. For example, in the case of bone tissue, the index BSI is compared with the mean structural index of the young population and/or with the value of the mean structural index of the population in the same age group as the patient.

According to embodiments the above-described steps can be implemented by a processing unit (16), of the type known in the art, optionally arranged remotely with respect to the place in which the patient's images are acquired or (FIG. 18) integrated in a measuring machine (1).

According to embodiments one or more of said pre-treatment sub-step (12A), ROI definition sub-step (12B), calculation sub-step (12C) and the calculation steps for calculating the mean values (13) and for calculating the representative index (14) can be performed automatically by image processing algorithms, and/or by visual learning techniques, for example by means of machine learning techniques of the type with neural networks.

In an embodiment the machine learning techniques can comprise both neural networks with "reinforcement" learning and convolutional neural networks, optionally in conjunction with fuzzy logic techniques.

According to an embodiment said pre-treatment sub-step (12A), ROI definition sub-step (12B), calculation sub-step (12C) and the calculation steps for calculating the mean values (13) and for calculating the representative index (14) can be designed according to a self-learning logic with neural networks at different levels of abstraction, organised through convolutional layers followed by a "pooling" layer, thanks to which the system can automatically learn functional relations between input data and output data, so as to be able to operate without having to resort to specially designed characteristics.

As previously explained, the invention also relates (FIG. 16, FIG. 17, FIG. 18) to a detection system made according to the present invention, which can be made in the form of a (FIG. 16, FIG. 17) portable measuring device (20) or of a (FIG. 18) measuring machine (1). Both the portable measuring device (20) and the measuring machine (1) will be suitable to acquire the images as explained with reference to the image acquisition step (10). While in the case of the measuring machine (1) the processing unit (16) can be integrated in the machine itself, in the case of the portable measuring device (20) the processing unit (16) can be an external device to which the portable measuring device (20) is to be connected or with which the portable measuring device (20) communicates by means of a respective wireless communication channel.

The detection system made in the form of a portable measuring device (20) comprises (FIG. 16, FIG. 17) a support base (21), on which the portable measuring device (20) rests in a stable way. The portable measuring device (20) comprises a handle (22) for the operator and a body (23), within which the X-ray emitting means are arranged. It should be noted that, in the embodiments illustrated (FIG. 16, FIG. 17), the support base (21) is shaped in such a way as to receive both the handle (22) and the body (23) resting on it. To this purpose, the support base (21) comprises a seat (24) for the handle (22).

The portable measuring device (20) also comprises (FIG. 16, FIG. 17) a screening element (25), such as a screening plate, which for example is circular. The screening element is shaped and oriented in such a way as to be able to screen the operator from the X-rays emitted by the X-ray emitting means during the image acquisition step (10).

According to an embodiment the central axis of symmetry of the screening element (25) is substantially aligned with a longitudinal axis of development of the body (23) of the portable measuring device (20).

In a different embodiment (FIG. 17) of the support base (21), the latter comprises a recess (26), shaped and positioned in such a way as to be able to receive an end portion of the body (23) resting on it. The detection system made in the form of a portable measuring device (20) also comprises X-ray detecting means, for example configured as a sensor element (27) to be applied on one finger of the individual to be subjected to tests, which can be built in a flexible band that can be wrapped around one finger and can be fastened in a stable way by releasable fastening means, such as adhesive means or tear-off fastening means.

Likewise (FIG. 18, FIG. 19, FIG. 20, FIG. 21), the detection system made in the form of a measuring machine (1) comprises X-ray emitting means as well. In the case of the measuring machine (1) the screening from radiation can be obtained by means of screening walls (3) fixed to a frame (2) of the machine. The screening walls (3) screen the outside of the machine in all directions, also providing flexible or movable and adaptable screening means for screening a slit (5) adapted for the insertion of the patient's hand to be examined. The screening of the measuring machine (1) is sized and oriented in such a way as to enable the screening of the individual being subjected to tests and of the environment surrounding the measuring machine (1) itself with respect to the X-rays emitted by the X-ray emitting means during the image acquisition step (10). The measuring machine (1) also comprises X-ray detecting means, for example configured as a sensor plate (19) that can be built in a support (28) of the measuring machine (1). In an embodiment the support (28) is fixed and is positioned inside the measuring machine (1). In a preferred embodiment of the present invention (FIG. 18, FIG. 19, FIG. 20, FIG. 21) the support (28) is slidingly fixed to the measuring machine (1) by means of sliding guides (29) in such a way that the support (28) realizes a carriage (17) that enables a movement of the support (28) between a first position (FIG. 19, FIG. 20) that is pulled-out with respect to an insertion slit (5) and a second position (FIG. 21) of insertion in which the support (28) is almost fully or fully inserted in the measuring machine (1). The insertion slit (5) is protected by a screening cover (18). By this solution it is possible to facilitate the positioning of the hand (37) of the individual to be subjected to tests, because the support (28) is fully visible in the first pulled-out position (FIG. 19, FIG. 20) and the hand's positioning can be facilitated by means of positioning lines (35) drawn on the support (28), it also being possible to resort to solutions of positioning lines (35) that are flat drawn lines or raised lines or resting surfaces whose shapes are adapted to the hand's shape. One can also provide solutions in which the positioning lines (35) are light lines lighting up the support (28) by means of backlighting or projection, for example by means of a laser projector. In this case, too, one can provide a band for fixing the hand in the optimal position on the support (28).

As far as both the detection system made in the form of a portable measuring device (20) and the detection system made in the form of a measuring machine (1) are concerned, the X-ray emitting means emit radiation that crosses the sample to be analysed, and of which a radiographic image has to be taken, and that is detected by the sensor element (27) or by the sensor plate (19), respectively.

With particular reference to the detection system made in the form of a portable measuring device (20), it needs an operator to be present and to handle the portable measuring device (20), and the operator must be a trained medical operator qualified for the use of the portable measuring device (20), such as a doctor or a radiology technician. Furthermore, the portable measuring device (20) must be necessarily used inside a closed room, although no specific room screening measure is required due to the tool's low emission.

However, there is the need in the market for large-scale availability at low costs of a detection system that is able to implement a method, which will be described in further detail hereinafter, for assessing the bone's trabecular component for the purpose of preventing and monitoring the risk of fragility fracture. In order to meet such requirement, it is necessary to provide an automatic tool able to eliminate the uncertainties and the variabilities connected to the operator. The detection system made in the form of a measuring machine (1) meets such requirement, because the measuring machine (1) can be easily positioned in different venues with respect to a medical or radiology centre. For example, the measuring machine (1) can be easily installed in easily accessible places spread over the territory, such as chemist's shops, OTC pharmacies or other places. Therefore, the measuring machine (1) is an integrated detection system able to automatically perform the operations of correct acquisition of the images and of calculation of the quality index of the bone structure. Such an apparatus can be directly activated by an operator locally with the operator present at the apparatus, or remotely with the operator remotely controlling the apparatus, or in a fully automatic way directly by the individual to be subjected to tests, optionally with remote control by an operator who checks the correctness of the operations performed by the individual to be subjected to tests. The method for calculating the quality index of the bone structure, BSI, will be explained in detail in the following of the present description. In particular, the value of the index BSI can be obtained, like in example 2, from the acquisition of the three images of the proximal epiphyses of the three central fingers of the non-dominant hand, or, in a simplified version, from the image of the proximal epiphysis of only one finger of the non-dominant hand.

In this embodiment the image acquisition system is enclosed in the measuring machine (1).

For example, the measuring machine (1) may look like an ATM machine. In order to obtain an image having a resolution suitable for reading, parameters compatible with the described measuring protocol and with the reference protocols for the sector will be provided.

The measuring machine (1) has a frame (2) provided with the previously described screening means in the form of screening walls (3). For example one can provide screening walls (3) able to contain the dispersion of the radiation produced on the inside, such as walls of polycarbonate charged with lead or metal with lead-sealed screening, depending on the position of the apparatus and on the presence or non-presence of an operator.

The measuring machine (1) is further provided with interface systems (4, 6, 8, 9, 15) for interfacing with the user.

For example, the measuring machine (1) can comprise an interactive touch-screen display (4). The measuring machine (1) can comprise a keyboard integrated in the touch-screen display (4) or an external control interface (6) can be provided, such as an external keyboard or push-button panel, for inputting the required data and for reading the information from the system to the individual to be subjected to tests who is being examined. For example, one can provide the input of anthropometric data or the confirmation of a non-pregnancy status or of the presence of risk factors.

A specific push-button (39) can be provided for starting measuring or measuring can be started by means of a control on the touch-screen display (4).

Furthermore, it will be possible to acquire images from a camera (38) inside the body of the machine framing the measuring zone for the display on the touch-screen display (4) to check the correct positioning of the hand (37) on the support (28). For example, one can provide a recognition step for recognising the hand's position in order to identify a non-correct positioning with respect to the sensor plate (19) and to communicate, by displaying them on the display (4), instructions for obtaining the optimal positioning for image acquisition.

Alternatively or in combination, one can also provide one or more visual inspection windows (7) protected by a lead-sealed transparent screen through which it is possible to check the hand's correct positioning.

For example the measuring machine (1) can comprise a document reader (8) such as a reader of a health insurance card or of a tax code card or of an identification card, able to univocally identify the individual to be subjected to tests being examined and to identify other individuals, if necessary, such as any operators or maintenance technicians.

For example, the measuring machine (1) can comprise a card reader (9) by means of insertion or wireless detection, such as by RFID or NFC technology, to perform service payment operations.

For example, the measuring machine (1) can comprise a scanner (15) for acquiring a medical prescription or a code authorising the required service.

As previously explained, the measuring machine (1) comprises a support (28) optionally realized on a carriage (17) sliding on guides (29). The carriage can be moved automatically by means of an electric motor (40).

The support can comprise positioning lines (35) or can be suitably shaped to facilitate the hand's correct positioning. One can also provide solutions for lighting up or backlighting the support (28) in order to facilitate the hand's (37) correct positioning. The support comprises a digital sensor plate (19) for acquiring images, of such dimensions as to ensure the acquisition of the image of the whole zone to be analysed (one or three proximal epiphyses).

Inside the structure of the measuring machine (1) one can also find:

An X-ray generation device, with settings predetermined as per protocol. The device does not contain on its inside any radioactive source, but the required field is generated only for the moment strictly required for acquisition (in the current protocol 0.17 seconds);

A processing unit (16), provided with a network interface card for remote connection for diagnostics or for the connection between the individual to be subjected to tests and an operator who connects remotely for example for an interview or for controlling remote operations or for transmitting the measuring results;

An optional camera (38) or, alternatively or in combination, inspection windows (7) optionally in combination with a mirror; the purpose of such devices is to check the hand's correct positioning on the support;

An optional printer (42) for issuing a medical report.

The patient accesses the structure and identifies himself/herself through his/her health insurance card or tax code card. The patient inputs the required data and then places his/her hand on the support with the help of the dotted lines in order to position the hand on the sensor correctly. In an embodiment the authorised technician is present and, after checking the hand's correct positioning through the display/camera, by means of a push-button activates the X-ray apparatus by generating the emission of the minimum radiation required for taking the X-ray scan. The acquired image is displayed on the display and, after being approved by the technician, is processed for generating the medical report.

In a further embodiment the authorised technician performs the described operations remotely.

In a further embodiment all the operations described are performed in a fully automatic way.

It will be clear that it is possible to modify or add parts or steps to the above-described method and system, without departing from the scope of the present invention.

It will also be clear that, although the present invention has been described with reference to a specific example, a person skilled in the art may realize many other embodiments for calculating an index representative of the mechanical properties of a material, all included in the scope of the present invention.

Two examples of application of the method according to the present invention will now be described and will have to be considered as illustrative both as far as the detection system made in the form of a portable measuring device (20) is concerned and as far as the detection system made in the form of a measuring machine (1) is concerned.

Example 1

Figure 3:
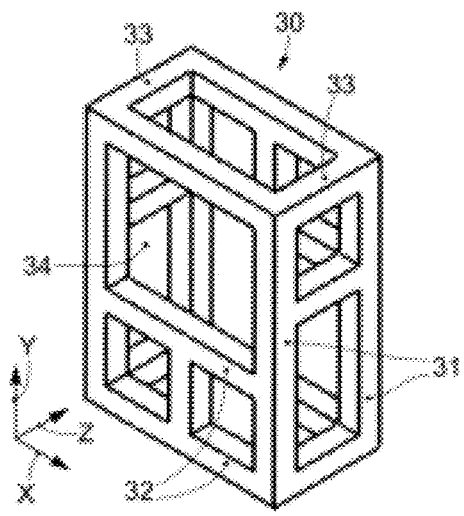
FIG. 3 and FIG. 5 are axonometric views of two examples of structures that can be analysed by means of the method according to the present invention.
Figure 5:
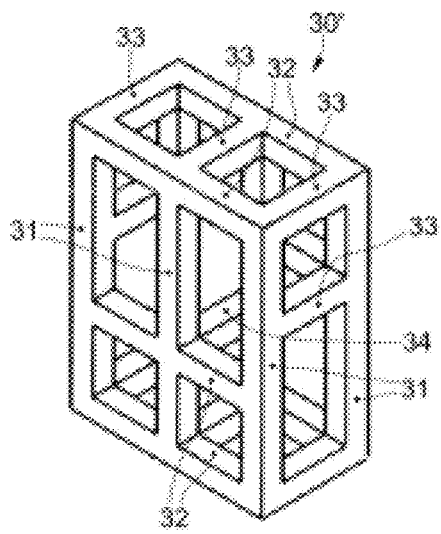

In the figures (FIG. 3, FIG. 5) one can see two different three-dimensional structures (30, 30') to be analysed by means of the method according to the present invention. The illustrative three-dimensional structures comprise a first three-dimensional structure (30) and a second three-dimensional structure (30').

It should be noted that the two different three-dimensional structures (30, 30') occupy the same overall volume and consist of a very similar number of elementary (geometric) units, and for this reason they are characterised by approximately equal density values but, as will be explained, their mechanical characteristics are much different from each other. This is due to the different arrangement in space of the structural elements, or elementary geometric units, included in the structure.

Each three-dimensional structure (30, 30') is made up of a plurality of elementary units (31, 32, 33) defining a three-dimensional matrix of uprights and crosspieces connected to one another. For example, a first elementary unit (31), a second elementary unit (32) and a third elementary unit (33) can be provided. According to an embodiment each three-dimensional structure (30, 30') comprises a plurality of first elementary units in the form of uprights (31), which extend parallel to a vertical direction Y, and a plurality of second elementary units (32) in the form of crosspieces and third elementary units (33) in the form of crosspieces. The crosspieces comprise:

- a first group of second elementary units (32) in the form of crosspieces, which extend substantially parallel to a horizontal direction X (width);
- a second group of third elementary units (33) in the form of crosspieces, which extend substantially parallel to a third direction Z (depth).

The directions X, Y and Z form a set of three Cartesian axes. Between the uprights (31) and the crosspieces (32, 33) in the three-dimensional structure (30, 30') a plurality of free spaces (34) is defined, that is to say, empty spaces in which the material is absent.

Figure 4:
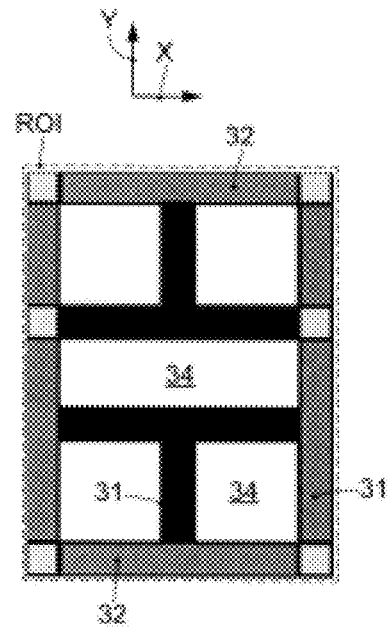
FIG. 4 and FIG. 6 are front views of an image acquired in an acquisition step by means of a detection system according to the present invention of the structures as in FIG. 3 and FIG. 5.

The above-described method according to the present invention allows to reconstruct a two-dimensional image (FIG. 4, FIG. 6) of the three-dimensional structures (30, 30') in which the different portions of the three-dimensional structure are depicted with different levels of grey, depending on their density. It should be noted that, as indicated by the dotted line in the figures (FIG. 4, FIG. 6), in this example the ROI substantially coincides with the external perimeter of the three-dimensional structures (30, 30'), according to the projection on the plane X-Y.

As it is known, a radiographic image allows to reproduce on a two-dimensional image also the contribution, in terms of density, of the phase considered arranged on the subsequent planes, which are parallel and arranged after the first one. In other words, the image of the figures (FIG. 4, FIG. 6) is inscribed in the plane X-Y and the different levels of grey are a function of the development of the structural elements in the plane Z, that is to say, in the depth direction.

Figure 6:
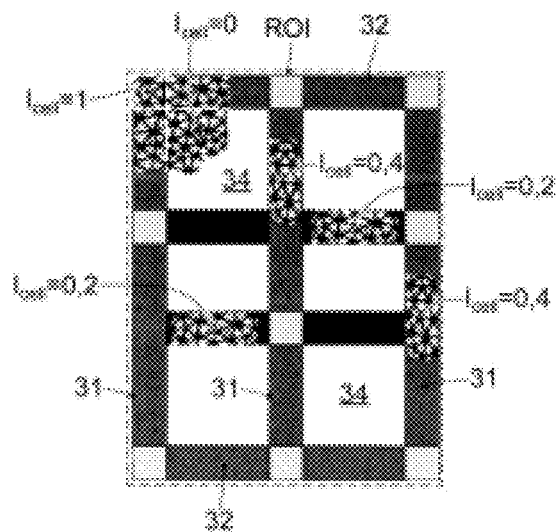

According to what is disclosed in U.S. Pat. No. 7,386,154 B2 a grid of cells, for example triangular, is superimposed to the image as in the figures (FIG. 4, FIG. 6), as it is schematically indicated in some portions of the figure (FIG. 6). A characteristic parameter ($I_{CELL}$) is assigned to each cell according to the phase present in the space occupied by the cell itself. For example, if a cell is arranged over one of said elementary units (31, 32, 33) or said free space (34), the characteristic parameter ($I_{CELL}$) of the cell will be equal to the assigned value (i.e., for example, 0, 0.2, 0.4, or 1). If a cell bridges two or more of said elementary units (31, 32, 33) or said free space (34), the characteristic parameter ($I_{CELL}$) will be calculated as the weighted average of the phases falling within that cell, with weights proportional to the surface of the cell occupied by the respective phase.

More in detail, in the example described herein, light grey indicates that, in correspondence of that portion, there is one of said elementary units (31, 32, 33), in particular a structural element (33) extending in an orthogonal direction with respect to the figure (parallel to the direction Z) and, therefore, it is a portion completely "full" with the phase considered. According to the method, a value of the characteristic parameter ($I_{CELL}$) amounting to 1 is associated with such colour. Smoke grey indicates the superimposition, one behind the other on planes parallel to the directrix X-Y and staggered along Z, of two of said elementary units (31, 32, 33) or structural elements, be they uprights (31) or crosspieces (32). According to the method, a value of the characteristic parameter ($I_{CELL}$) amounting to 0.4 is associated with such colour. Black indicates the presence of only one of said elementary units (31, 32, 33) or structural elements, be it an upright (31) or a crosspiece (32). According to the method, a value of the characteristic parameter ($I_{CELL}$) amounting to 0.2 is associated with such colour. Finally, according to the method, a value of the characteristic parameter ($I_{CELL}$) amounting to 0 is associated with each free space (34), in correspondence of which the phase is completely absent, such free spaces not contributing to the mechanical characteristics of the structure.

The results of the third processing step (12) of the method according to the present invention provide the following.

As far as the first three-dimensional structure (30) is concerned (FIG. 3), one obtains an apparent elastic modulus (E*) amounting to 202 MPa, and an apparent elastic modulus (E*) amounting to 228 MPa calculated on the basis of the model constructed by the above-described cell method starting (FIG. 4) from the two-dimensional image. With such values the index BSI, calculated according to what is disclosed in the present invention, amounts to 174.

As far as the second three-dimensional structure (30') is concerned (FIG. 5), one obtains an apparent elastic modulus (E*) amounting to 251 MPa, with a 20% variation with respect to the previous structure, and an apparent elastic modulus (E*) amounting to 289 MPa calculated on the basis of the model constructed by the above-described cell method starting (FIG. 6) from the two-dimensional image, with a 21% variation with respect to the previous structure.

With such values the index BSI, calculated according to what is disclosed in the present invention, amounts to 225, with a 23% variation with respect to the previous structure, greater than the variation detected with reference to the elastic modulus. Therefore, the method according to the present invention allows to emphasize the differences between structures having analogous density, by means of a numerical index that is readily and easily interpreted and that facilitates the classification thereof.

Example 2

In this example the method according to the present invention is used to assess the structural resistance of the bone tissue of an individual to be subjected to tests.

Figure 7:
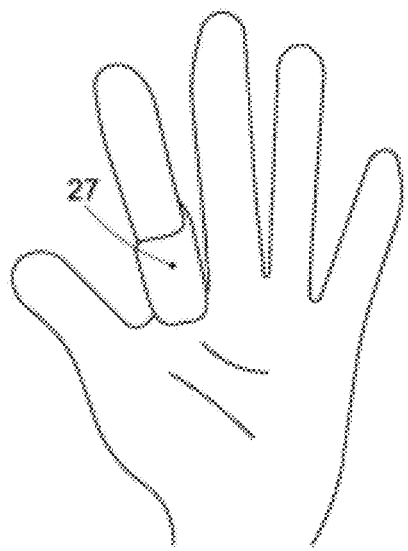
FIG. 7, FIG. 8, FIG. 9 are schematic front views of a patient's hand arranged to perform a first image acquisition step of the method according to the present invention, wherein one can see sensor means associated with three different fingers, respectively.
Figure 8:
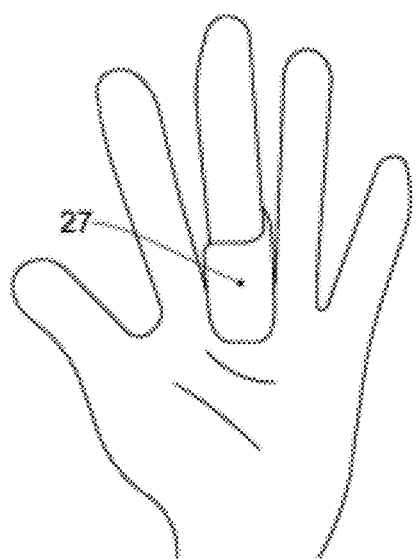
Figure 9:
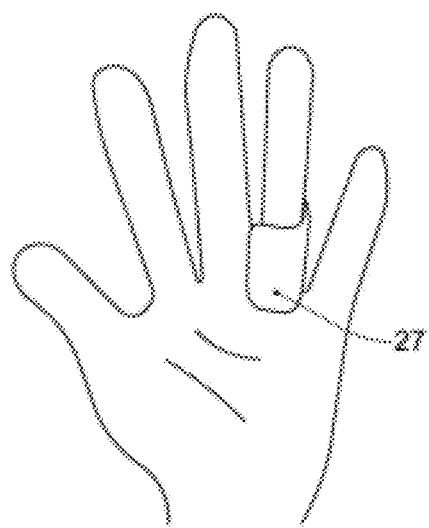

In the first acquisition step (10) three images of respective anatomical sites of an individual to be subjected to tests are acquired. In this example the chosen anatomical sites are the first phalanges of the index (FIG. 7), middle (FIG. 8) and ring finger (FIG. 9), respectively. In this case (FIG. 7, FIG. 8, FIG. 9) the left hand of an individual to be subjected to tests is shown, wherein, in correspondence of the first phalanx the digital sensor (27), built in a flexible band wrapped around the finger, is arranged.

Three radiographic images of the first proximal epiphysis of the three central fingers (index, middle, ring finger) of the non-dominant hand of an individual to be subjected to tests are then acquired, in accordance with what has been previously disclosed in the present invention.

In an embodiment the acquired images are radiograms, for example acquired by means of a detection system according to the present invention, which can be a detection system made in the form (FIG. 16, FIG. 17) of a portable measuring device (20) or made in the form (FIG. 18, FIG. 19, FIG. 20, FIG. 21) of a measuring machine (1). As a non-exhaustive example, the portable measuring device (20) can be the device called NOMAD Pro 2™ marketed by Aribex, or the device called EzRay Air™ marketed by Vatech.

According to embodiments during the first acquisition step (10) the exposure parameters are kept constant and are related to the type of device used.

In an embodiment the digital sensor (27) can be a sensor of the known type, such as the sensor called GXS700™ marketed by Gendex™ or EZ Sensor Classic™ Slim marketed by Vatech.

Two sets of three radiographic images acquired in the first acquisition step (10) are shown in FIG. 10, FIG. 11, FIG. 12 and FIG. 13, FIG. 14, FIG. 15, respectively.

In each of these Figures the square box indicates the region of interest in which the planned processing is carried out. It should be noted that this is the largest square area that is fully inscribed in the trabecular zone of the bone phase being analysed.

We would like to point out that, by suitably enlarging the ROIs, it would be possible to highlight the bone structures in which the trabeculae are substantially oriented like the elementary units (31, 32, 33) or structural elements and like the free spaces (34) of the previously discussed example (FIG. 3, FIG. 4, FIG. 5, FIG. 6). In other words, in these anatomical sites, the trabeculae are oriented on parallel planes (lying on the plane directrix X-Y) reciprocally connected by trabeculae mainly arranged in a direction that is orthogonal to these planes, the trabeculae extending parallel to the third direction Z (depth). The method advantageously provides a rotation step for rotating the image(s) acquired after the image acquisition step and before the parameter ($I_{CELL}$) acquisition step. The rotation step consists of a rotation by such a quantity that an orientation of the structure of the bone tissue is substantially parallel to Cartesian axes forming said elementary geometric elements. In this way one of the plane directrices X-Y, according to which the trabeculae are oriented, coincides with the axes of the elementary units (31, 32, 33) or structural elements, in particular with the axes of uprights (31) and crosspieces (32, 33), in the structure (30, 30').

In this case, too, like in the above-described previous example, the structural elements forming the structure comprise portions depicted with different levels of grey, which, as already said, take into account the quantity of the considered phase arranged in the depth direction Z. As stated above, a different value of the characteristic parameter ($I_{CELL}$) is associated with each level of grey, by re-processing which according to the method disclosed in the above-mentioned U.S. Pat. No. 7,386,154 B2 shortly mentioned again above, it is possible to obtain the results below.

Figures 10, 11, 12:
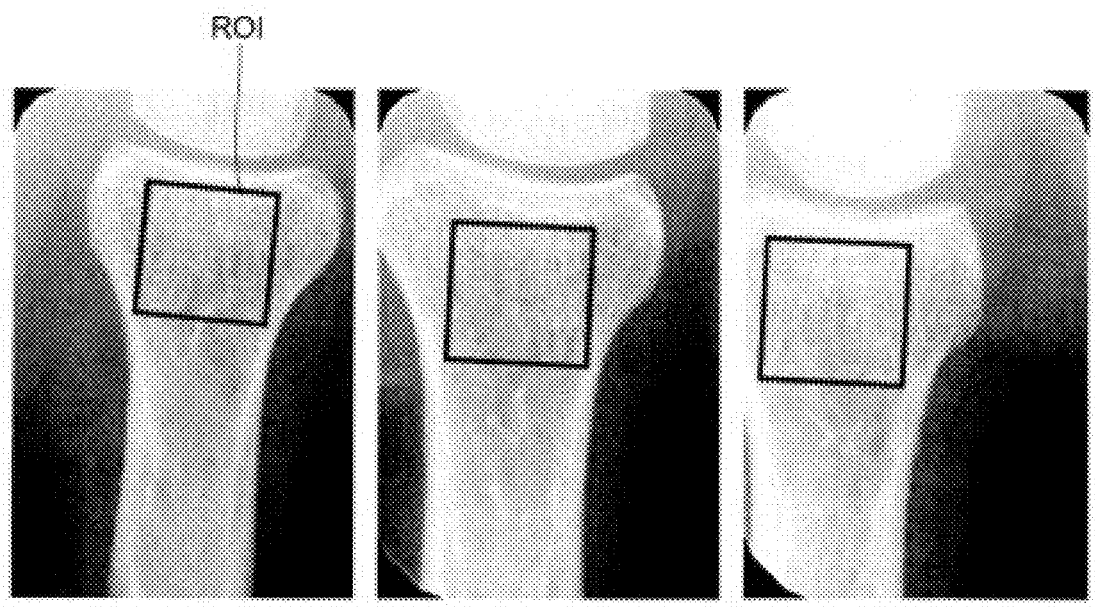
FIG. 10, FIG. 11, FIG. 12 are an example of radiologic images of a portion of the fingers of FIG. 7, FIG. 8, FIG. 9, respectively, acquired by means of the detection system according to the present invention.

As far as the bone structure as in FIG. 10, FIG. 11, FIG. 12 is concerned, one obtains an apparent elastic modulus (E*) amounting to 588 MPa, which is the result of the mean of the six values $E_x^*$, $E_y^*$, calculated for the three images acquired. With such values the index BSI, calculated according to what is disclosed in the present invention, amounts to 154.

Figures 13, 14, 15:
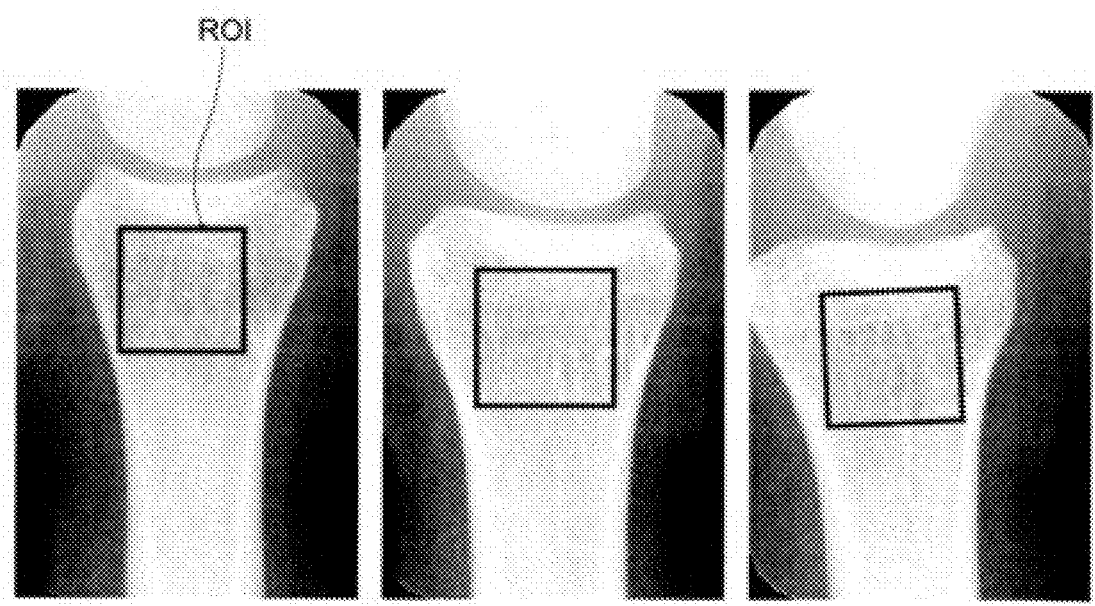
FIG. 13, FIG. 14, FIG. 15 are a further example of radiologic images of a portion of the fingers of FIG. 7, FIG. 8, FIG. 9, respectively, acquired by means of the detection system according to the present invention.

As far as the bone structure as in FIG. 13, FIG. 14, FIG. 15 is concerned, one obtains an apparent elastic modulus (E*) amounting to 604 MPa, which is the result of the mean of the six values $E_x^*$, $E_y^*$, calculated for the three images acquired. With such values the index BSI, calculated according to what is disclosed in the present invention, amounts to 194.

The first set of radiographic images was acquired from the non-dominant hand of a female individual to be subjected to tests, aged eighty-three, whose bone structure is essentially "weak" due to old age.

The second set of radiographic images was acquired from the non-dominant hand of a female individual to be subjected to tests, aged twenty-five, whose bone structure is "resistant" as expected from the individual's young age.

The method according to the present invention allows to emphasize the quality of the bone structure by means of a numerical index that is readily and easily interpreted.

In fact, it should be noted that, against a difference by about 2% between the apparent elastic moduli (E*) calculated on the basis of the first and of the second set of radiographic images, the corresponding index BSI shows a difference by about 20% in both cases.

The present invention has been described with reference to the figures enclosed in a preferred embodiment thereof, but it is evident that many possible changes, modifications and variants will be readily understood by a person skilled in the art in the light of the previous description. Thus, it should be noted that the present invention is not limited to the present description, but it includes any changes, modifications and variants in compliance with the appended claims.

NOMENCLATURE USED

With reference to the identification numbers in the enclosed figures, the following nomenclature has been used:
1. Measuring machine
2. Frame
3. Screening wall
4. Display
5. Slit
6. Control interface
7. Inspection window
8. Document reader
9. Card reader
10. Image acquisition step
11. Image validation step
12. Image processing step
12A. Image pre-treatment sub-step
12B. ROI definition sub-step
12C. Calculation sub-step for calculating the elastic module and characteristic coefficient
13. Calculation step for calculating the mean value of BSI
14. Calculation step for calculating the index BSI
15. Scanner
16. Processing unit
17. Carriage
18. Cover
19. Sensor
20. Portable measuring device
21. Support base
22. Handle
23. Body
24. Seat
25. Screening means
26. Recess
27. Sensor
28. Support 29. Guide
30. First three-dimensional structure
30'. Second three-dimensional structure
31. First elementary unit
32. Second elementary unit
33. Third elementary unit
34. Free space
35. Positioning lines
36. Movement direction
37. Hand
38. Camera
39. Push-button
40. Motor
41. X-ray generation device
42. Printer

We claim:

1. A method of calculating an index representative of properties of monophase or multiphase material in which the monophase or multiphase material is a bone of an individual to be tested by a detection system in which the detection system has a processing unit and an x-ray generating device, the x-ray generating device emitting x-rays following an activation command, the detection system having a screening device configured to screen a user or an operator from the x-ray generating device, the detection system having a sensor configured to be used with a sample of the monophase or multiphase material from a desired anatomical site to be analyzed, the sensor detecting the x-rays emitted by the x-ray generating device, the method comprising:

acquiring at least one image by the sensor of the sample of the monophase or multiphase material, the at least one image allowing a distinguishing from each other one or more phases inside a closed region of interest;

generating cells of elementary geometric elements which are superimposed on the at least one image by said processing, unit;

acquiring by said processing unit a parameter for each of the cells in association a region of interest, the parameter being indicative of a presence or absence in the cell of the phase considered, wherein if the phase is present, the parameter is proportional to a quantity of the phase present in the cell;

processing the at least one image by said processing unit so as to calculate a density coefficient of the monophase or multiphase material as a function of characteristic values for each of the cells, the density coefficient being calculated on the value of the parameter of the phase falling within the cell, wherein the density coefficient is a value calculated as a sum of the parameters for each region of interest;

calculating a value of elastic modules by stimulation of behavior under load from application modules in which a mechanical behavior an internal structure of the region of interest is simulated, wherein each cell contributes to the value of apparent elastic modules and the parameter;

calculating an index representative of properties of the monophase or multiphase material, the index being proportional to the value of the apparent elastic modules net of a contribution of the density coefficient;

rotating an image acquired after the step of acquiring at least one image and before the step of acquiring the parameter, the rotating being an amount of rotation such that an orientation of a structure of the monophase or multiphase material is substantially parallel to a Cartesian axis of the elementary geometric elements, wherein the step of acquiring at least one image requires three image samples, wherein the step of preparing is repeated for each of the three images so as to obtain at least one value of the apparent elastic modules and one value of the density coefficient for each of the three images, wherein the step of acquiring at least one image acquires three digital radiographic images in an anterior/posterior projection of the first proximal epiphysis respectively of an index finger and a middle finger and a ring finger of a non-dominant hand of an individual to be tested in correspondence with a trabecular structure, the trabecular structure being trabeculae oriented according to planar parallel to each other and to directrix in staggered in succession one after another and connected by further trabeculae arranged along a third direction; and calculating the index averaged over the number of images acquired from the three-dimensional radiographic images of the index finger and the middle finger and the ring finger of the non-dominant hand, the index being indicative of a quality of a bone structure.

2. The method of claim 1, wherein the index is calculated according to the following formula:

$$BSI=f[f_1(E^*)-f_2(C)]$$

in which f, $f_1$ and $f_2$ are functions that are different from each other, and in particular;

f is a function of an exposure parameters used during a first image acquisition step;

$f_1$ and $f_2$ are functions whose result is a constant positive such that the result of $f_2$ is subtracted from $f_1$ in such a way as to obtain a subtraction of a contribution due to the density of material to the contribution due to the elastic modulus.

3. The method of claim 1, wherein the index is calculated according to the following formula:

$$BSI=a_1(b_1E^*-b_2C)$$

wherein:

E* the apparent elastic modulus (apparent Young's modulus), and

C is the density coefficient, $a_1$ is a value function of exposure parameters used during the image acquisition step;

$b_1$ and $b_2$ are positive constants, in such a way as to obtain a subtraction of a contribution due to the density of the material to the contribution due to the elastic modulus.

4. The method of claim 1, wherein the monophase or multiphase material is formed by a plurality of elementary units defining a three-dimensional matrix of uprights and crosspieces connected to one another, the method further comprising:

pre-treating the images after the step of acquiring the at least one image so as to filter the at least one image.

5. The method of claim 4, further comprising;

defining the region of interest as a largest square or rectangular area fully inscribed in the sample.

6. The method of claim 5, wherein the step of processing and pre-treating and defining and calculating respective mean values and calculating the index are automatically performed by image processing algorithms or by machine learning techniques for neural-networks.

7. The method of claim 1, wherein the step of acquiring at feat one image is performed by a portable device provided with a handle for an operator, which is connected to a body within which the X-ray emitting device is are arranged and with which said screening device is associated, the detection system further comprising a support base configured to support said portable device, said sensor comprising an X-ray digital sensor having a flexible band wrapped around one finger of the individual.

8. The method of claim 1, wherein the step of acquiring at least one image is performed by a measuring machine provided with a frame having screening walls wherein the measuring machine comprises the X-ray emitting device, the measuring machine comprising a support for resting one hand of the individual to be subjected to tests, the measuring machine cooperating with the X-ray emitting, device to acquire the at least one image of the sample of the monophase or multiphase material, the sensor being a sensor plate for detecting the X-rays emitted by the X-ray emitting device.

9. A detection system for detecting images of the sample using the method of claim 1, wherein the detection system is a portable device having a handle for an operator, which is connected to a body within which the X-ray emitting devices is arranged, the detection system having a support base configured to support said portable device and the sensor.

10. The detection system of claim 9, wherein the support base comprises at least one seat or a recess shaped and positioned in such a way as to be able to receive at least one of either the handle or the body resting on it so as to set a position of the portable device.

11. The detection system for detecting images of the sample using the method of claim 1, wherein the detection device is a measuring machine provided with a frame having screening walls, wherein the measuring machine comprises the X-ray emitting device, the measuring machine comprising a support for resting one hand of the individual to be tested, the measuring machine further comprising the sensor in the form of a sensor plate for detecting the X-rays emitted by the X-ray emitting device.

12. The detection system of claim 11, wherein the support is selected from the group consisting of positioning lines drawn on the support wherein the positioning lines are flat, light positioning lines lighting up the support by means of backlighting or projection, positioning lines arranged on the support wherein the positioning lines are raised, resting surfaces having shapes corresponding to a shape of the hand, and a band for fixing the hand in the optimal position on the support.

13. The detection system of claim 11, wherein the support is steady and is positioned inside the measuring machine, and the sensor plate being integrated on the surface of said support.

14. The detection system of claim 11, wherein the support is fixed to the measuring machine in a sliding way by sliding guides in such a way that the support has a carriage that enables a movement of the support between a first position that is pulled-out with respect to an insertion slit and a second position in which the support is or fully inserted in the measuring machine.

15. The detection system of claim 14, wherein the sensor plate for is integrated on the surface of the support.

16. The detection system of claim 14, wherein the insertion slit is protected by a screening cover.

17. The detection system of claim 11, wherein the measuring machine has a processing unit for calculating an index representative of the properties of the monophase or multiphase material.

18. The detection system of claim 11, wherein the measuring machine has a connector adapted for the remote connection with an operator.

19. The detection system of claim 11, wherein the measuring machine includes interface systems for interfacing with the individual to be subjected to tests.

20. The detection system of claim 19, wherein the measuring machine includes one or more interface systems selected from the group consisting of an interactive touch-screen display, a control interface in the form of a keyboard or push-button panel, a push-button for starting measuring, a document reader for reading documents in the form of identification cards of the individual to be subjected to tests, and a payment card reader to perform service payment operations, a scanner for acquiring a medical prescription, and a code authorizing the required service.

21. The detection system of claim 20, wherein the measuring machine includes a camera that frames the measuring zone for displaying on a display to check a correct positioning of the hand on the support.

22. The detection system of claim 21, further comprising:
a display that displays the measuring zone framed by the camera, the display being an interactive touch-screen display.

23. The detection system of claim 11, wherein the measuring machine includes one or more visual inspection windows protected by a lead-sealed transparent screen.

24. The detection system of claim 11, wherein the measuring machine includes a printer.

* * * * *